(12) United States Patent
Rhee et al.

(10) Patent No.: US 8,586,099 B2
(45) Date of Patent: Nov. 19, 2013

(54) METHOD FOR PREPARING A PRION-FREE BOND GRAFTING SUBSTITUTE

(75) Inventors: Sang-Hoon Rhee, Seoul (KR); Choong-Pyoung Chung, Seoul (KR); Yoon-Jeon Park, Seoul (KR)

(73) Assignee: Seoul National University Industry Foundation, Seoul (KR)

( * ) Notice: Subject to any disclaimer, the term of this patent is extended or adjusted under 35 U.S.C. 154(b) by 864 days.

(21) Appl. No.: 12/299,799

(22) PCT Filed: May 12, 2006

(86) PCT No.: PCT/KR2006/001773
§ 371 (c)(1),
(2), (4) Date: Mar. 13, 2009

(87) PCT Pub. No.: WO2007/132952
PCT Pub. Date: Nov. 22, 2007

(65) Prior Publication Data
US 2009/0304807 A1    Dec. 10, 2009

(51) Int. Cl.
*A61K 35/32* (2006.01)
(52) U.S. Cl.
USPC ........................................................ 424/549
(58) Field of Classification Search
None
See application file for complete search history.

(56) References Cited

U.S. PATENT DOCUMENTS

| 4,619,989 | A | * | 10/1986 | Urist | 530/417 |
| 5,167,961 | A | | 12/1992 | Lussi et al. | |
| 5,306,302 | A | * | 4/1994 | Bauer et al. | 623/23.63 |
| 5,417,975 | A | | 5/1995 | Lussi et al. | |
| 2006/0014283 | A1 | * | 1/2006 | Yim et al. | 435/379 |

OTHER PUBLICATIONS

Wenz et al, Biomaterials, 2001, vol. 22, pp. 1599-1606.*
Broz, J.J., et al., Effects of deproteinization and ashing on site-specific properties of cortical bone, Jounal of Materials Science: Materials in Medicine, 1997, pp. 395-401, vol. 8, Chapman & Hall.

* cited by examiner

*Primary Examiner* — Allison Ford
(74) *Attorney, Agent, or Firm* — Tristan A. Fuierer; Andrew D. Gerschutz; Moore & Van Allen, PLLC

(57) ABSTRACT

The present invention relates to a method for preparing a bone graft substitute using bovine bone, and more particularly to a method for preparing a safe bone graft substitute which does not have the risk of infection with bovine spongiform encephalopathy, the method comprising treating bovine bone with sodium hypochlorite and treating the treated bone at a high temperature of more than 600° C. The bone graft substitute does not cause an immune response, because it is prepared by effectively removing lipids and organic substances from bovine bone having a structure very similar to that of the human bone. Also, it has excellent osteoconductivity, and is free of prion, and thus it does not have the risk of infection with bovine spongiform encephalopathy. According to the disclosed invention, the bone graft substitute having such advantages can be prepared in a simple manner.

3 Claims, 4 Drawing Sheets

(a) Bio-Oss, 2 weeks (b) OsteografN, 2 weeks (c) Examples 1, 2 weeks (a) Bio-Oss, 4 weeks (b) OsteoGrafN, 4 weeks (c) Examples 1, 4 weeks

US 8,586,099 B2

METHOD FOR PREPARING A PRION-FREE BOND GRAFTING SUBSTITUTE

CROSS-REFERENCE TO RELATED APPLICATIONS

This application is filed under the provisions of 35 U.S.C. §371 and claims the priority of International Patent Application No. PCT/KR2006/001773 filed on 12 May 2006 entitled "Method for Preparing a Prion-Free Bone Grafting Substitute" in the name of Sung-Hoon Rhee, et al., which is hereby incorporated by reference herein in its entirety.

TECHNICAL FIELD

The present invention relates to a method for preparing a bone graft substitute using bovine bone, and more particularly to a method for preparing a safe bone graft substitute which does not have the risk of infection with bovine spongiform encephalopathy, the method comprising treating bovine bone with sodium hypochlorite and treating the treated bone at a high temperature of more than 600° C.

BACKGROUND ART

A bone graft substitute (BGS) refers to a graft material that is used to substitute for bone tissue defects caused by various dental diseases or traumas, disease-related degeneration or other loss of tissue, so as to fill pore spaces in the bone tissue and to promote the formation of new bone. The best graft is generally known to be autogenous bone graft, but the autogenous bone graft has problems in that it requires a secondary surgical operation, is difficult to obtain the required amount, is difficult to carry out at small-scale hospitals, and has a possibility that makes patient's pain and morbidity severe.

For this reason, various substitutes, including donated human bones, artificial bones, and artificially synthesized materials made of bone hydroxyapatite, have been used for grafting. Commercially available bone substitutes are advantageous in that they are available in various forms, including powder, gel, slurry/putty, tablets, chips, morsels, pellets, sticks, sheets and blocks, are homogeneous, have a low risk with respect to infection and disease, eliminate the risk of pains resulting from the collection of a patient's own bones for grafting, and have reduced limitations on size. However, these commercial bone substitutes have various problems. For example, because their structure is significantly different from the physical structure of human bone, they have a slow tissue regeneration rate.

In an attempt to solve these problems, bone minerals obtained by physicochemically treating animal bones having a structure similar to that of human bones so as to remove organic substances have been processed such that they could be used in dental or orthopedic surgical operations. A typical example thereof may include Bio-Oss® commercially available from Geistlich Biomaterials.

A method for preparing said bone graft substitute using animal bones comprises the steps of: treating the thighbone of a bovine animal in a solvent having a boiling point of 80-120° C. to remove lipids; adding ammonia or primary amine to the treated bone to remove proteins and organic substances, thus obtaining bone mineral; and heating the bovine mineral at a high temperature of 250-600□ for a few hours, followed by drying (U.S. Pat. Nos. 5,167,961 and 5,417,975).

Although there was an example where a cartilage was treated with sodium hypochlorite to selectively remove the collagen phase in order to observe the remaining cartilage structure (Broz, J. J. et al., *J. Mater. Sci. Mater. Med.*, 8:395, 1997), it has not yet been reported that sodium hypochlorite is used to remove all proteins in the preparation of bone minerals.

Among such animal bones, the most frequently used bone is bovine bone, and said Bio-Oss® product is also produced using the bovine bone as a raw material. However, as the onset of bovine spongiform encephalopathy has recently been frequent, the safety of the bovine bone as a raw material with respect to bovine spongiform encephalopathy is not ensured. For this reason, in a step of processing bovine bone into a bone graft material, a prion that causes bovine spongiform encephalopathy must be removed. Because the prion is not completely removed even at a high temperature of 600° C., it cannot be removed by methods known so far, and thus the development of a novel method is required.

Accordingly, the present inventors have prepared a bone graft substitute, which does not have the risk of bovine spongiform encephalopathy, using a method comprising the steps of inactivating prion protein with sodium hypochlorite in a process of preparing a bone graft substitute using bovine bone, and heating the resulting bone at a high temperature of 600° C., thereby completing the present invention.

SUMMARY OF INVENTION

In one aspect, the present invention relates to a method for preparing a bone graft substitute, which is completely free of prion protein that causes bovine spongiform encephalopathy, the method comprising treating bovine bone with sodium hypochlorite and heating the treated bone at a high temperature.

In another aspect, the present invention relates to a bone graft substitute composition containing the bone graft substitute prepared according to said method.

Other features and embodiments of the present invention will become apparent from the following detailed description and claims.

DETAILED DESCRIPTION OF THE INVENTION AND PREFERRED EMBODIMENTS

Figure 1:
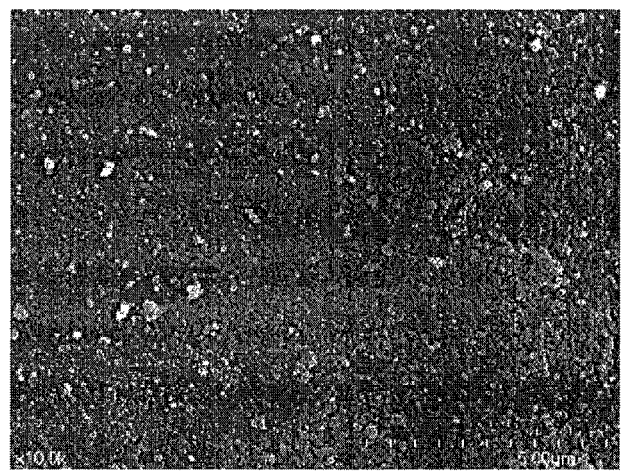
FIG. 1 is a scanning electron microscope photograph of bone powder thermally treated at 600° C.

The present invention provides a method for preparing a bone graft substitute from bovine bone, the method comprising the steps of: (a) boiling bovine bone, from which blood components have been removed, in deionized water to remove lipids and proteins, and drying the boiled bone; (b) grinding the dried bone, and immersing and shaking the ground bone powder in an organic solvent; (c) removing the organic solvent and drying the bone powder; (d) treating the dried bone powder, from which the solvent has been removed, with a solution of 2-20% sodium hypochlorite; (e) removing the sodium hypochlorite solution from the bone powder and drying the resulting bone powder; and (f) thermally treating the dried bone powder at 600-1000° C. for 1-6 hours to completely remove lipids and proteins.

In the inventive method, the step of immersing the bone powder in the organic solvent is a step of removing lipids remaining in the bovine bone powder, in which the organic solvent may preferably be a mixed solvent of chloroform and methanol. The ratio of chloroform:methanol in the mixed solvent may be 2-8:8-2, and preferably 1:1.

In the inventive method, the step of treating the bone powder with the sodium hypochlorite solution is a step of removing proteins remaining in the bovine bone powder and inactivating a prion that causes bovine spongiform encephalopathy. The sodium hypochlorite solution used in this step may be a solution having a sodium hypochlorite concentration of 2-20% (w/v), and most preferably about 4% (w/v). The step of treating the bone powder with the sodium hypochlorite must be conducted for at least 20 minutes in order to inactivate the prion, and is preferably conducted for at least 72 hours in order to remove the remaining proteins.

In the inventive method, the step (d) may additionally comprise adding 1-10N sodium hydroxide to the sodium hypochloride solution in order to increase efficiency of inactivating the prion. The concentration of the sodium hydroxide is preferably about 2N.

The inventive method may additionally comprise, after the step (f), the steps of: sieving the thermally treated bone powder through a sieve having a pore size of 212-425 μm; and washing the sieved bone powder.

In another aspect, the present invention provides a composition for bone graft substitution, containing the bone graft substitute prepared according to said method.

The inventive composition for bone graft substitution may additionally contain at least one biologically active substance selected from the group consisting of a bone growth-promoting factor, a fibrin, a bone morphogenic factor, a bone growth agent, a chemotherapeutic agent, an antibiotic, an analgesic, a bisphosphonate, a strontium salt, a fluorine salt, a magnesium salt, and a sodium salt. Also, it may additionally contain at least one chemical compound selected from the group consisting of hyaluronic acid, chondroitin sulfate, alginic acid, chitosan, collagen, hydroxyapatite, calcium carbonate, calcium phosphate, calcium sulfate, and ceramics.

In still another aspect, the present invention provides a gel-type composition for bone graft substitution, in which said chemical compound is hyaluronic acid.

As used herein, the term "bone graft substitute" refers to a material for filling spaces in bone tissue. The bone graft substitute can be used in the form of putty; paste, formable strips, blocks, chips, etc., which are formed by compressing, compacting, pressably contacting, packing, squeezing or tamping the bone powder into the desired shape. Also, it can be used in the form of gel, granules, paste, tablets, pellets, etc., which are formed using chemical additives, and it can be used in a powder form as it is.

If the bone graft substitute is used in the above-described forms, it is preferable to add biologically active substances thereto. Examples of the biologically active substances, which can be used in the present invention, include a bone growth-promoting factor, a fibrin, a bone morphogenic factor, a bone growth agent, a chemotherapeutic agent, an antibiotic, an analgesic, a bisphosphonate, a strontium salt, a fluorine salt, a magnesium salt, and a sodium salt.

Examples of the growth factor, which can be used in the present invention, include BMP (bone morphogenic protein), PDGF (platelet-derived growth factor), TGF-beta (transgenic growth factor), IGF-I (insulin-like growth factor), IGF-II, FGF (fibroblast growth factor) and BGDF-II (beta-2-microglobulin). Examples of the bone morphogenic factor, which can be used in the present invention, include osteocalcin, bonesialo protein, osteogenin, BMP and the like. The bone growth agent can be used without any particular limitation as long as it is harmless to the human body and promotes bone growth. Examples of the bone growth agent, which can be used in the present invention, include peptides or nucleic acids that facilitate bone formation, and antagonists for substances that inhibit bone formation.

Examples of chemical additives, which are used to form the bone graft substitute in the present invention, include hyaluronic acid, chondroitin sulfate, alginic acid, chitosan, collagen, hydroxyapatite, calcium carbonate, calcium phosphate, calcium sulfate, and ceramics. Depending on the kind of the additives, the bone graft substitute can be formed in the shape of gel, strips, granules, chips, pellets, tablets, paste, etc.

EXAMPLES

Hereinafter, the present invention will be described in further detail with reference to examples. It is to be understood, however, that these examples are for illustrative purposes only and are not to be construed to limit the scope of the present invention.

Example 1

Preparation of Bone Graft Substitute

[Pretreatment and Grinding Step]

A bovine femoral bone was cut to a size of 5 cm$^3$ using a bone cutter. The cut bone pieces were immersed in deionized water for 24 hours to remove blood components present in the bone. The bone pieces washed with deionized water were boiled for 72 hours while replacing the deionized water at 12-hr intervals, thus primarily removing lipids and proteins present in the bones. The bone pieces from which the lipids and proteins have primarily been removed were completely dried in an oven at 60° C. for 24 hours, and then ground to a size of less than 0.7 mm using a mill.

[Defatting Step]

To 1 g of the ground bone powder, 20 ml of a mixed solvent of chloroform and methanol (1:1 v/v) was added and the solution was shaken at a rotating speed of 120 rpm for 24 hours so as to defat the bone powder. In order to remove the solvent remaining in the defatted bone powder, deionized water was added to the bone powder in a weight ratio of 50:1, and then the solution was shaken at 120 rpm for 12 hours, thus removing the solvent remaining in the powder. At this time, the deionized water was replaced with fresh deionized water at 2-hr intervals in order to increase washing efficiency. The washed bone powder was completely dried in an oven at 60° C.

[Deproteinizing Step]

To 1 g of the defatted bone powder, 25 ml of a solution of 4% (w/v) sodium hypochlorite was added and the powder solution was shaken at a rotating speed of 120 rpm for 24 hours so as to remove proteins present in the bone and to inactivate a prion that causes bovine spongiform encephalopathy. In order to remove the solvent present in the deproteinized bone powder, 50 g of deionized water was added to 1 g of the bone powder, and the solution was shaken at 120 rpm for 72 hours, thus removing the sodium hypochlorite remaining in the powder. At this time, the deionized water was replaced with fresh deionized water every two hours for the first 12 hours, and then replaced with fresh deionized water every 12 hours. The water-washed bone powder was completely dried in an oven at 60° C.

[Thermal Treatment Step]

The defatted, deproteinized and dried bone powder was thermally treated at high temperature to remove lipids and proteins remaining therein. The temperature of an electric furnace used for the thermal treatment was elevated at a rate of 2° C./min, and the bone powder was thermally treated at 600° C. for 3 hours, followed by furnace cooling.

[Sieving Step]

The thermally treated bone powder was sieved through a sieve having a pore size of 215-425 μm, and the sieved bone powder was washed a few times with deionized water to remove fine particles remaining on the surface thereof, and then dried in an oven at 60° C. for 24 hours. The dried bone powder was collected and used as a bone graft substitute.

Figure 2:
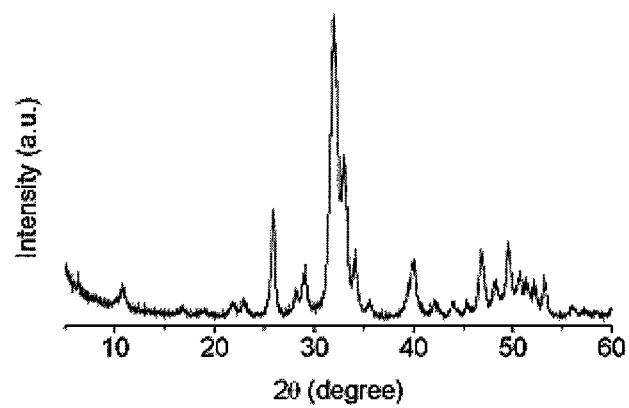
FIG. 2 shows XRD measurement results for bone powder thermally treated at 600° C.
Figure 3:
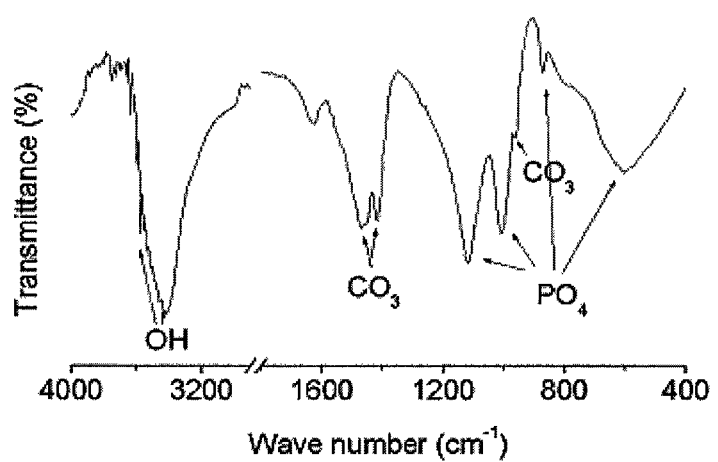
FIG. 3 shows FT-IR measurement results for bone powder thermally treated at 600° C.

The bone powder subjected to the above-described steps was analyzed using a scanning electron microscope and, as a result, hydroxyapatite particles having a size of 50-80 nm were observed in the bone powder (FIG. 1). Also, the bone powder was analyzed by XRD and, as a result, it could be observed that a pure, low crystalline apatite phase was produced in the bone powder (FIG. 2). Also, from the results of FT-IR analysis, it was confirmed that the bone powder was a low crystalline carbonate apatite containing a carbonate group, similar to human bone (FIG. 3).

Example 2

Preparation of Composition for Bone Graft Substitution

To 100 g of desalted water, 20 g of hyaluronic acid was added to make a viscous hyaluronic acid solution, to which 10 g of the bone powder prepared in Example 1 was then added to make an injectable paste.

Example 3

Evaluation of Osteoconductivity of Bone Graft Substitute

In order to examine the osteoconductivity of the inventive bone graft substitute, the evaluation of osteoconductivity was conducted for the bone graft substitute prepared according to the method of Example 1, and commercially available bone substitutes Bio-Oss® and OsteoGraf®/N as control groups. In this Example, New Zealand white rabbits were used and circular defects having a diameter of 8 mm were formed in the cranial bones of the animals and then implanted with each of the inventive bone graft substitute, Bio-Oss® and OsteoGraf®/N granules. At 2 weeks and 4 weeks after the implantation, tissue samples were prepared and comparatively analyzed for osteoconductivity on the basis of the amount of bone produced around each of the bone graft substitutes and the production or non-production of connective tissues.

Figure 4:
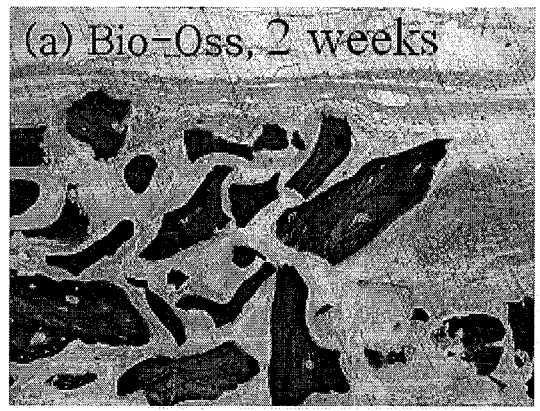
FIG. 4 shows photographs of tissue samples taken at 2 weeks after each of bone powder prepared in Example 1, Bio-Oss®, and OsteoGraf®)/N has been implanted into the circular defects of New Zealand white rabbits.
Figure 4:
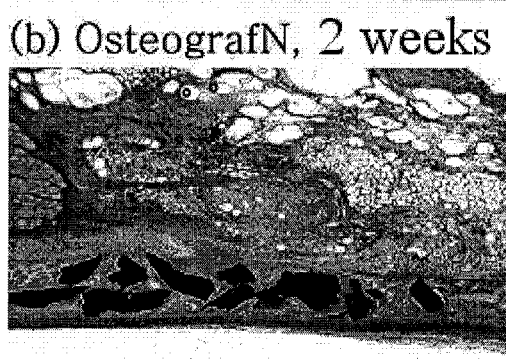
Figure 4:
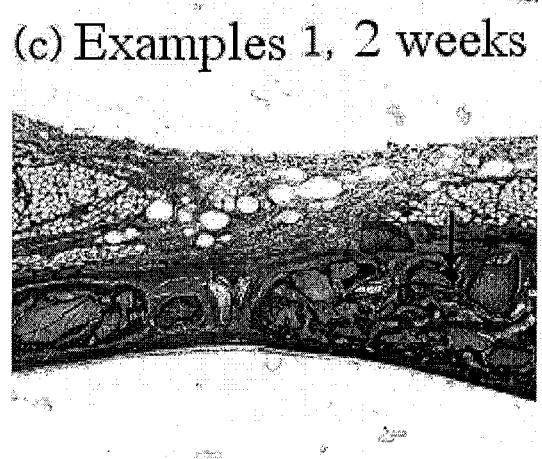

As a result, in the test samples prepared at 2 weeks after implantation of the three bone substitutes, only connective tissues were mostly produced around the portions implanted with Bio-Oss® and OsteoGraf®/N, and the formation of new bones was hardly observed around the implanted portions (FIG. 4). On the other hand, as shown in FIG. 4(c), it could be observed that the sample implanted with the bone graft substitute prepared in Example 1 had a large amount of new bones produced therein (see arrow in FIG. 4(c)).

Figure 5:
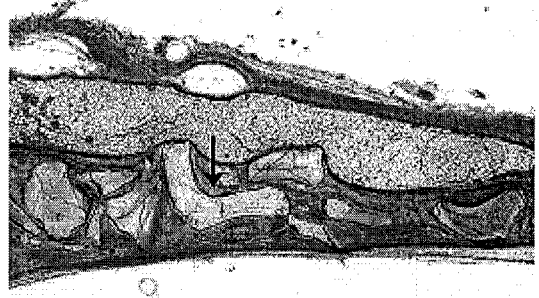
FIG. 5 shows photographs of tissue samples taken at 4 weeks after each of bone powder prepared in Example 1, Bio-Oss®, and OsteoGraf®)/N has been implanted into the circular defects of New Zealand white rabbits.
Figure 5:
Figure 5:
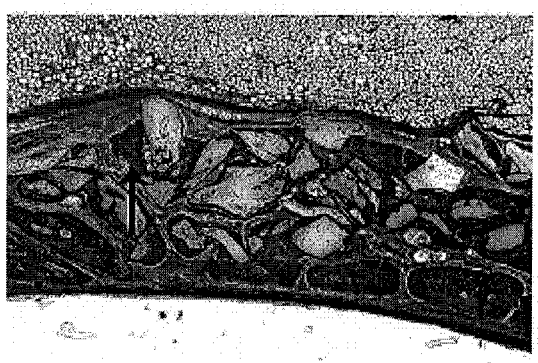

FIG. 5 shows photographs of tissue samples prepared at 4 weeks after implantation with the three bone substitutes. As shown in FIG. 5, in the tissue samples implanted with Bio-Oss® and OsteoGraf®/N, a very small amount of new bones were formed and mostly surrounded by connective tissues, and on the other hand, in the tissue samples implanted with the bone graft substitute prepared in the Example 1, a large amount of new bones were produced and grown around the bone graft substitute. This suggests that the bone graft substitute prepared according to the present invention has very excellent osteoconductivity compared to those of the prior bone graft substitutes.

INDUSTRIAL APPLICABILITY

As described above, the present invention provides the method for preparing the prion-free bone graft substitute, comprising treating bovine bone with sodium hypochlorite solution and subjecting the treated bone to high-temperature treatment, as well as a composition containing said bone graft substitute. The inventive bone graft substitute does not cause an immune response, because it is prepared by effectively removing lipids and organic substances from bovine bone having a structure very similar to that of the human bone. Also, it has excellent osteoconductivity, and is free of the prion, and thus it does not have the risk of infection with bovine spongiform encephalopathy. According to the present invention, the bone graft substitute having such advantages can be prepared in a simple manner.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:
1. A method for preparing a bone graft substitute from bovine bone, the method comprising the steps of:
 (a) boiling bovine bone, from which blood components have been removed, in deionized water to remove lipids and proteins;
 (b) drying the boiled bone;
 (c) grinding the dried bone to a powder;
 (d) immersing and shaking the ground bone powder in an organic solvent;
 (e) drying the bone powder to remove the organic solvent;
 (f) treating the dried bone powder, from which the solvent has been removed, with a solution comprising 4-20% (w/v) sodium hypochlorite to inactivate prion protein;
 (g) removing the sodium hypochlorite solution from the bone powder;
 (h) drying the resulting bone powder from which the sodium hypochlorite has been removed; and
 (i) thermally treating the dried bone powder of step (h) at 600-1000° C. for 1-6 hours to completely remove lipids and proteins.

2. The method for preparing a bone graft substitute from bovine bone according to claim 1, wherein the organic solvent is a mixed solvent of chloroform and methanol.

3. The method for preparing a bone graft substitute from bovine bone according to claim 1, which further comprises the steps after the step (i): sieving the thermally treated bone powder through a sieve having a pore size of 212-425 μm; and
washing the sieved bone powder.

* * * * *